United States Patent [19]

Rosequist

[11] 4,058,119

[45] Nov. 15, 1977

[54] WALKING DEVICE

[76] Inventor: Craig D. Rosequist, Box 265, Star Route, Mesa, Wash. 99343

[21] Appl. No.: 706,543

[22] Filed: Aug. 12, 1976

[51] Int. Cl.² .............................................. A61F 3/00
[52] U.S. Cl. ...................................... 128/80 R; 3/4; 128/83.5
[58] Field of Search ................ 128/80 R, 80 F, 80 G, 128/83, 87 R, 83.5; 3/2, 4, 15, 17

[56] References Cited

U.S. PATENT DOCUMENTS

| 51,593 | 12/1865 | Jewett | 3/17 R |
|---|---|---|---|
| 875,482 | 12/1907 | Wyatt | 3/2 |
| 1,257,284 | 2/1918 | Elters | 3/15 |
| 2,678,054 | 5/1954 | Bostelman | 3/17 R X |
| 3,058,120 | 10/1962 | Smith et al. | 3/4 |
| 3,070,807 | 1/1963 | Wheeler | 3/4 |
| 3,660,920 | 5/1972 | Spina | 3/4 X |

Primary Examiner—John D. Yasko
Attorney, Agent, or Firm—Robert Keith Sharp

[57] ABSTRACT

A walking device for use by a person having an injured foot or ankle comprises a standard reaching from the ground to approximately the waist of the wearer and an elongated knee and shin support extending at right angles to the standard. A strap on the standard encircles the thigh and a strap on the knee and shin support encircles the calf. The upper end of the standard passes beneath a belt which loosely encircles the waist. For ease in sitting, the lower portion, or support piece, of the standard is made so as to be collapsible. In one embodiment, it is hinged to the upper portion, or thigh piece. In a second embodiment, the support piece and the thigh piece are in telescopic relationship. In each embodiment there are releasable locking means for holding the support piece against collapse while walking.

10 Claims, 16 Drawing Figures

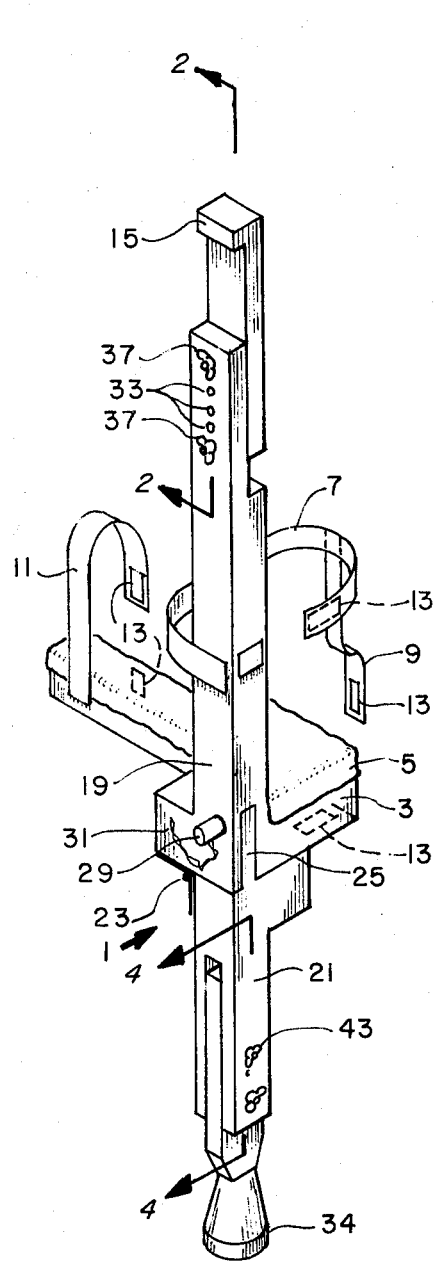
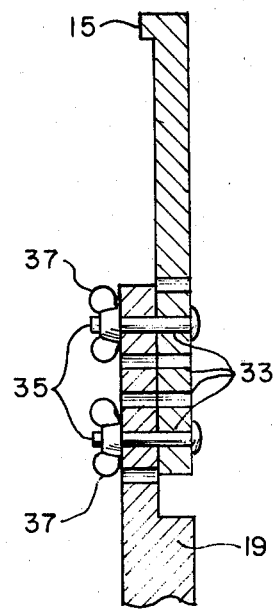
Fig. 2
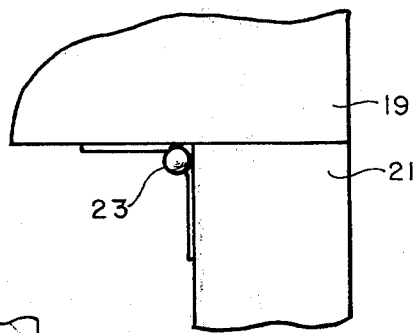
Fig. 3
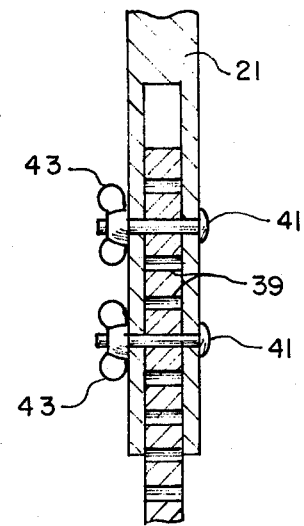
Fig. 4
Fig. 1

U.S. Patent  Nov. 15, 1977  Sheet 4 of 4  4,058,119
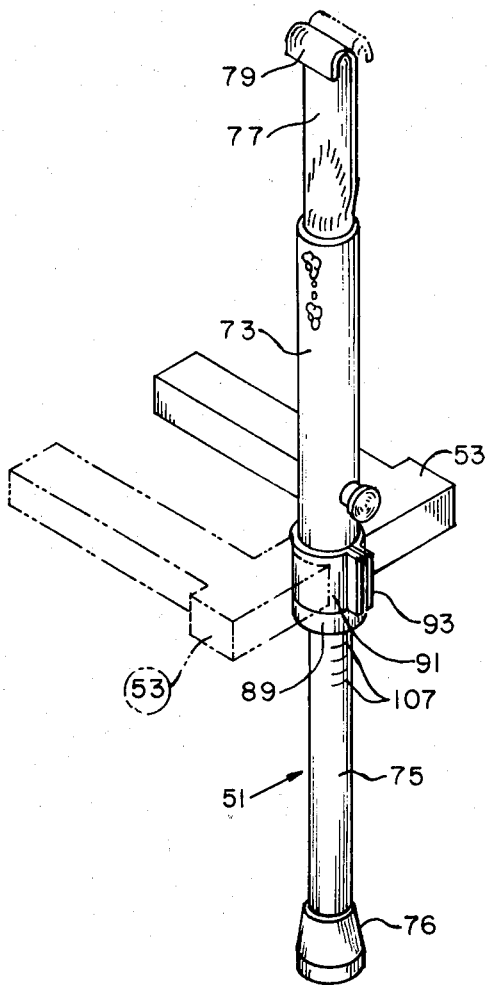
Fig. 8
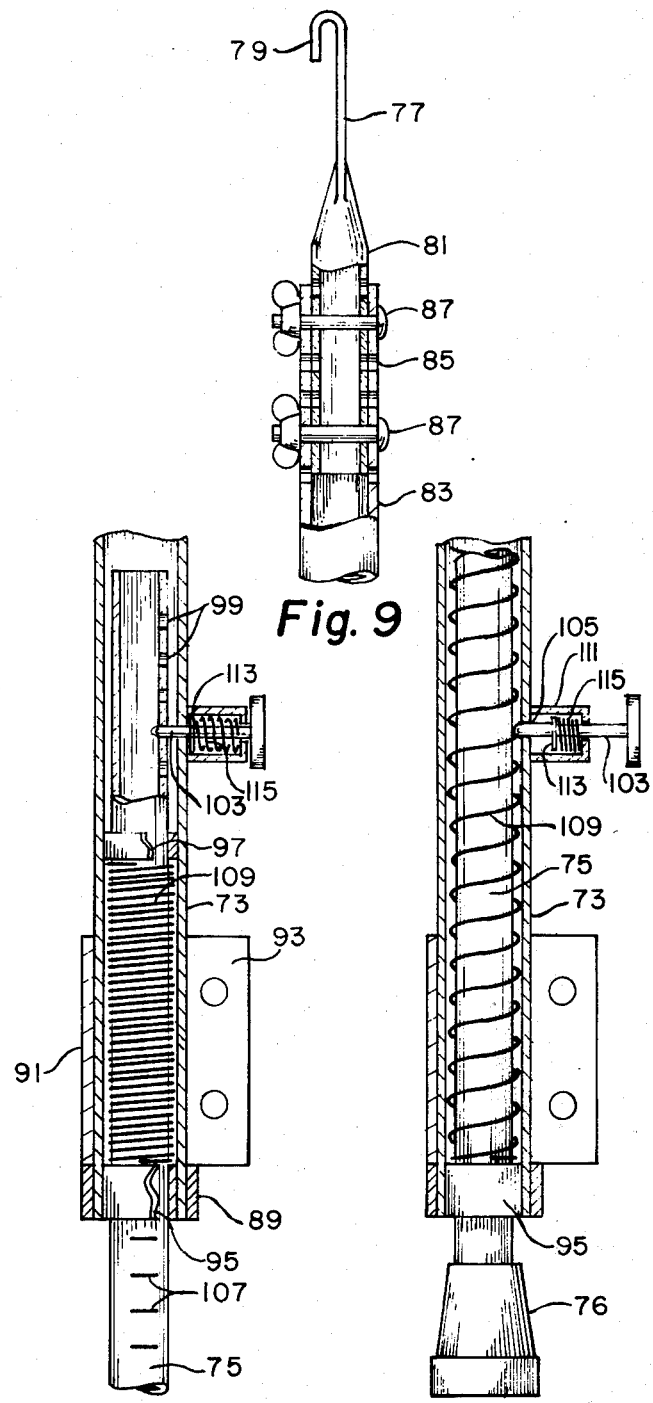
Fig. 9
Fig. 10
Fig. 11
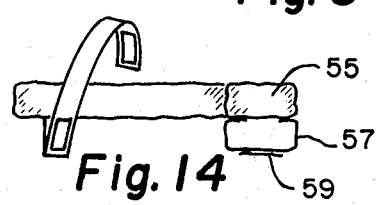
Fig. 14
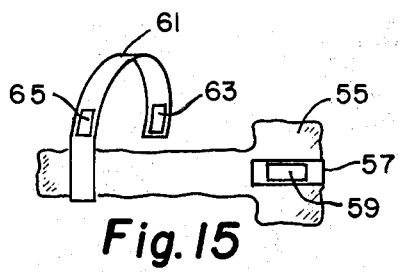
Fig. 15
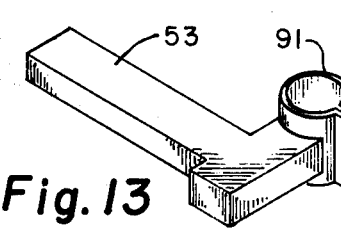
Fig. 13
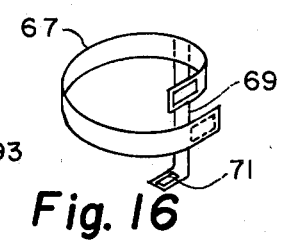
Fig. 16

WALKING DEVICE

INTRODUCTION

This invention relates to a device for use by a person having an injured foot or ankle which will permit walking with far less discomfort and inconvenience than crutches, which leaves both hands free while walking and which can preferably be partially collapsed so as not to interfere with sitting in a chair or a car. The device can be worn while driving a car having an automatic transmission. The device is particularly suitable for use by a person wearing a "short" cast covering the lower leg. I have found it possible to put in an entire day of manual work while wearing the device.

SUMMARY OF THE INVENTION

Basically, the device comprises two members—a standard which extends from the ground to approximately the wearer's waist and an elongated knee and shin support which extends at right angles to the standard. In use, the wearer's leg is bent at the knee, with the knee and shin resting on the knee and shin support. Straps on the standard encircle the wearer's thigh and other straps on the knee and shin support encircle the calf. The upper end of the standard passes beneath a belt which loosely encircles the wearer's waist. This restrains movement toward and away from the wearer's body and improves stability.

For ease in sitting, the lower portion, or support piece, of the standard is preferably made so as to be collapsible. In one embodiment, it is hinged to the upper portion, or thigh piece, and provided with releasable locking means. When the wearer is seated, he releases the locking means. The support piece then hangs vertically beside the chair or other seat, out of the way. In the other embodiment, the support piece is telescopic relative to the thigh piece.

Adjustment means are provided on the thigh piece and support piece for fitting the device to persons of different heights and bodily proportions.

DESCRIPTION OF THE DRAWINGS

In the drawings:

FIG. 1 is a perspective view of a first embodiment of my invention.

FIG. 2 is a fragmentary sectional view of the upper portion of the embodiment in FIG. 1, taken on the line 2—2, FIG. 1.

FIG. 3 is a fragmentary side view of the middle portion of the embodiment of FIG. 1.

FIG. 4 is a fragmentary sectional view of the lower portion of the embodiment of FIG. 1, taken on the line 4—4, FIG. 1.

FIG. 8 is a perspective view of a second embodiment of my invention.

FIG. 9 is a fragmentary view, partially in section, of the upper portion of the embodiment of FIG. 8.

FIG. 10 is a fragmentary view, partially in section, of the central portion of the embodiment of FIG. 8, showing the support piece in an extended position.

FIG. 11 is a fragmentary view, partially in section, of the central portion of the embodiment of FIG. 8 showing the support piece in a retracted position.

FIG. 13 is a perspective view of a knee and shin support for the embodiment of FIG. 8.

FIG. 14 is a side view of a cushion for the knee and shin support of FIG. 13.

FIG. 15 is a bottom view of the cushion of FIG. 14.

FIG. 16 is a perspective view of a thigh strap for the embodiment of FIG. 8.

DETAILED DESCRIPTION

I have shown two embodiments of my invention, that of FIGS. 1-7, which is made principally of wood, and that of FIGS. 8-16, which is made principally of metal. The choice of one or the other embodiment will be governed largely by the mode of manufacture normally employed by the maker.

FIRST EMBODIMENT

The embodiment of FIGS. 1-7 will be described first.

Figure 5:
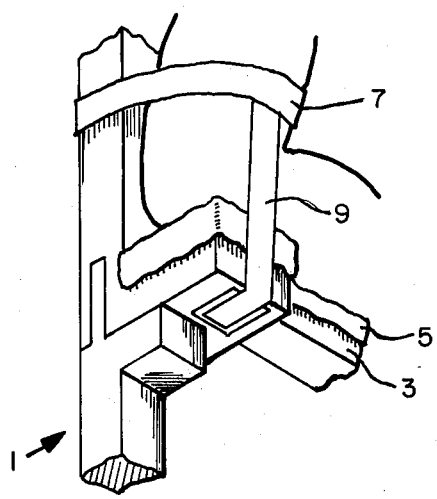
FIG. 5 is a perspective view of a knee and shin support and thigh strap of the embodiment of FIG. 1.
Figure 6:
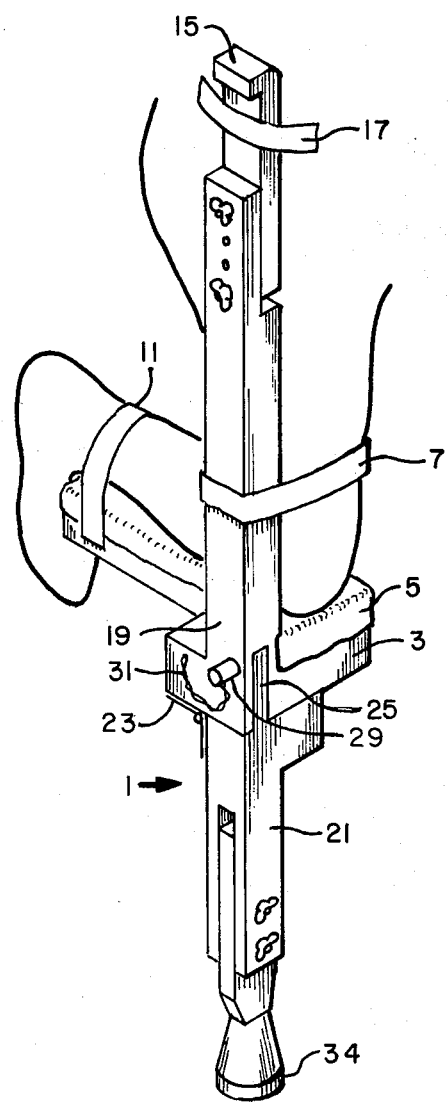
FIG. 6 is a perspective view showing the embodiment of FIG. 1 in use with the wearer standing.

Referring to FIGS. 1, 5 and 6, the device includes a standard 1 and a knee and shin support 3 secured to the standard at right angles thereto, substantially at knee height from the ground. As shown in FIG. 6, standard 1 is of such length as to reach from the ground substantially to the wearer's waist. The knee and shin support is elongated, as shown, so as to extend from the kneecap to the ankle, and is preferably provided with a pad 5.

A thigh strap 7 is connected to standard 1 a short distance above the knee and shin support. A support strap 9 connects thigh strap 7 to knee and shin support 3. A calf strap 11 is connected to the outer portion of knee and shin support 3.

In use, as shown by FIGS. 5 and 6, thigh strap 7 encircles the wearer's thigh, and calf strap 11 encircles the lower calf or ankle. Support strap 9 transmits a lifting force to knee and shin support 3 and helps to control standard 1 when the leg is raised in walking. Preferably the cooperating surfaces carry strips 13 of hook and loop adhering fabric, such as that sold under the name "Velcro." Alternatively, the straps can be provided with buckles.

At the upper end of standard 1 is a belt-engaging hook formed by a ledge 15. In use, the wearer's waist is encircled by a loosely fitting belt 17 (FIG. 6) which passes over standard 1 beneath the ledge 15. This restrains lateral movement of standard 1 relative to the wearer's body and greatly improves stability. Ledge 15 prevents the belt 17 from slipping off the end of standard 1.

Figure 7:
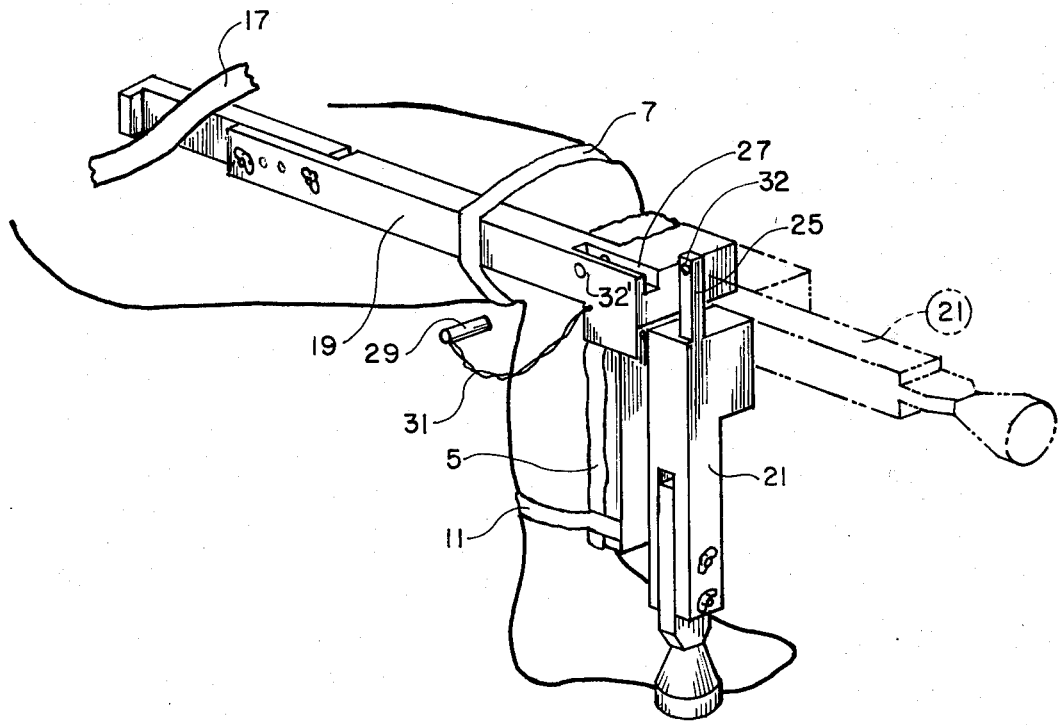
FIG. 7 is a perspective view showing the embodiment of FIG. 1 in use with the wearer seated.
Figure 12:
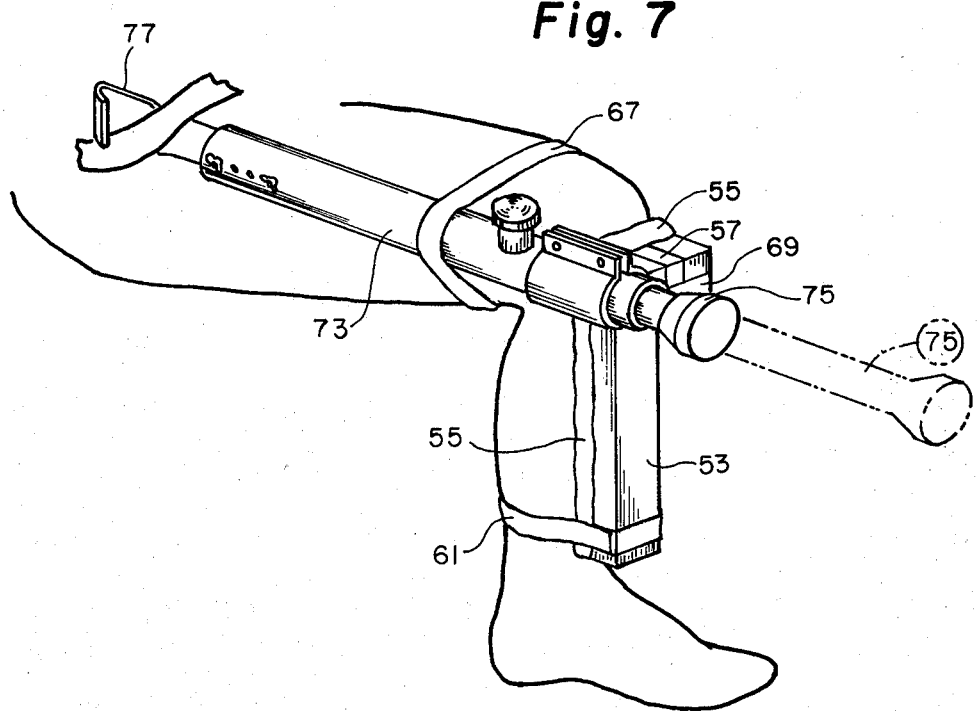
FIG. 12 is a perspective view showing the embodiment of FIG. 8 in use, with the wearer seated.

Standard 1 comprises an upper thigh piece 19 and a lower support piece 21, joined by a hinge 23 (see FIGS. 1 and 3). As best shown in FIG. 7, support piece 21 includes a tongue 25 which fits in a socket 27 formed in thigh piece 19. A removable pin 29, preferably secured to a strap or thong 31, passes through cooperating bores 32, 32¹ formed in tongue 25 and thigh piece 19, respectively. Support piece 21 terminates in foot piece 34.

When the wearer sits down, support piece 21 is initially in the position shown in broken lines in FIG. 7. The wearer then withdraws pin 29 and lowers support piece 21 to the position shown in solid lines, where it is out of the way of passersby. The wearer can sit reasonably comfortably in a car and he can drive a car having an automatic transmission.

Both the thigh piece 19 and the support piece 21 are made adjustable as to length in order to accommodate wearers of different heights and bodily proportions. Thigh piece 19 is made of two adjoining parts, and provided with a series of holes 33 (see FIG. 2) through which bolts 35, provided with wing nuts 37 may be selectively passed. Similarly, lower support piece 21 is made of two interfitting parts provided with holes 39 (see FIG. 4) through which bolts 41, provided with wing nuts 43, may selectively be passed.

SECOND EMBODIMENT

The second embodiment, shown in FIGS. 8-16, is functionally much the same as the embodiment just described, but is made of tubular metal and has differences in structure and mechanical operation resulting from the change in material.

Referring to FIG. 8, this embodiment comprises a standard 51 and a knee and shin support 53 extending at right angles thereto. As will be explained later, the knee and shin support can be shifted from the position shown in solid lines, for use on the right leg, to that shown in broken lines, for use on the left leg.

A removable cushion 55 (FIGS. 14 and 15) is provided for shin support 53. This cushion is provided on its bottom with a loop 57, either made of elastic material or provided with lacing, which may have affixed to it either the "loop" of "hook" member 59 of an adherent fabric pair, such as that sold under the name "Velcro." A strap 61 encircles the lower calf of the wearer and knee and shin support 53 (see FIG. 12). It is preferably provided with strips 63, 65 of adherent fabric, but may instead carry a buckle. A thigh strap 67 (FIGS. 12 and 16) carries a support strap 69 which connects at its lower end to web 57, as by adherent fabric strip 71, which cooperates with strip 59 on loop 57.

Standard 51 comprises two telescoping members, an upper thigh piece 73 and a lower support piece 75 terminating in foot piece 76. At the upper end of thigh piece 73 is a belt-engaging hook member 77 which terminates in a ledge 79. The lower portion 81 of hook member 77 is cylindrical and fits within the main body portion 83 of thigh piece 73. Members 81 and 83 are pierced by a series of holes 85 through which are passed bolts 87. This permits adjustment of the length of thigh piece 73 or the complete removal of hook member 77.

A support sleeve 89 surrounds and is attached to the lower end of thigh piece 73. Knee and shin support 53 also includes a support sleeve 91. When in use, sleeve 91 rests on sleeve 89, thus supporting knee and shin support 53.

Sleeve 91 is split and provided with flanges 93. It exerts a clamping action on thigh piece 73. This may be obtained either by forming it as a spring or by providing bolts through flanges 93.

To change knee and shin support 53 from the "right leg" position shown in solid lines to the "left leg" position shown in broken lines, hook member 77 is removed. Sleeve 91 is spread to pass housing 111, the function of which will be explained later, and slid off thigh piece 73. Cushion 55 is removed, knee and shin support 53 is then turned upside down and sleeve 91 is then slid over thigh piece 73 until it is again resting on sleeve 89. Cushion 55 is then replaced on what is now the top, previously the bottom, of knee and shin support 53. Hook member 77 is turned to the position shown in broken lines in FIG. 8.

As in the first embodiment, the lower support piece is made selectively collapsible relative to the thigh piece, so that it is out of the way when the wearer is seated. Instead of being hinged, as in the first embodiment, it is in telescopic relationship with the upper thigh piece and, preferably, a spring is arranged to retract it when desired.

One such arrangement is shown in FIGS. 10 and 11. Lower support piece 75 is telescopically mounted within upper thigh piece 73. There is a first guide ring 95 fixed to the inside of thigh piece 73 and a second guide ring 97 on the outside of support piece 75. A pin 103 passes through a corresponding hole 105 in thigh piece 73 and enters one of the holes 99 in support piece 75, holding the latter in the extended position, the effective length being governed by the particular hole selected. Since the holes 99 are not visible, it may be desirable to provide indicia 107 on the exposed portion of support piece 75 to make it easier to select the proper exposed length each time. Having the correct length is important for the stability of the wearer.

While support piece 75 and pin 103 may be manually moved in both directions, I prefer that they be spring-biased. A spring 109 is mounted in compression between guide ring 95, on thigh piece 73, and guide ring 97, on support piece 75. It tends to move the latter from its extended position, FIG. 10, to its retracted position, FIG. 11.

Pin 103 is mounted in housing 111 fixed to thigh piece 73. A disc 113 is secured to pin 103 and a spring 115 is compressed between disc 113 and housing 111.

The operation of the collapsible feature in this embodiment is as follows.

Assume the wearer has been walking on the device with pin 103 engaging one of the holes 99. He then sits down, with the member 75 in the broken line position of FIG. 12. He then pulls out on pin 103, releasing support piece 75, which is pushed to its retracted position, shown in solid lines, by spring 109 (FIGS. 10 and 11). Pin 103 now frictionally engages the unperforated portion of support piece 73, which tends to prevent undesired movement.

When the wearer wishes to stand, he again pulls out pin 103, pushes support piece out to the correct position, as shown by indicia 107, and allows pin 103 to enter the corresponding hole 99.

While I have described two embodiments in detail, it will be apparent that various changes can be made. I therefore wish my invention to be limited solely by the scope of the appended claims.

I claim as my invention:
1. A walking device comprising:
a standard of such length as to reach from the ground substantially to the wearer's waist,
an elongated knee and shin support extending substantially at right angles to said standard substantially at knee height, of such length as to extend substantially from the knee cap to ankle of the wearer,
at least one strap on said standard above said knee and shin support for encircling the wearer's thigh,
and at least one strap on said knee and shin support horizontally spaced from said standard for encircling the wearer's calf,
said standard comprising:
a thigh piece extending upwardly from said knee and shin support and a support piece extending downwardly from said knee and shin support, said support piece and said thigh piece being joined in a manner such that said support piece is quickly collapsible relative to said thigh piece, while remaining attached thereto, to a position such that when the wearer is seated the support piece does not extend substantially beyond said knee and shin support, and manually quickly releasable locking means for locking said support piece against collapse.

2. A walking device as defined in claim 1, wherein said standard comprises a belt-engaging hook at its upper end.

3. A walking device as defined in claim 1 wherein said knee and shin support comprises a padded upper supporting surface.

4. A walking device as defined in claim 1, said thigh piece and said support piece being adjustable as to length.

5. A walking device as defined in claim 1 comprising a hinge connecting said thigh piece and said support piece, said support piece being freely swingable on said hinge when said locking means is released.

6. A device as defined in claim 5 wherein said thigh piece and said support piece comprise mutually interfitting end members, and said locking means comprises a pin passing through holes in said end members.

7. A walking device as defined in claim 1 wherein said support piece is in telescopic relationship with said thigh piece and is slidable between an extended position and a retracted position in which it does not extend substantially beyond said knee and shin support.

8. A walking device as defined in claim 7 wherein said locking means comprises a pin passing through holes in said thigh piece and said support piece.

9. A walking device as defined in claim 8, wherein said support piece comprises a longitudinally spaced series of holes which said pin may selectively enter to adjust the effective length of said support piece in its extended position.

10. A walking device as defined in claim 7 and further comprising a spring within said thigh piece engaging said thigh piece and said support piece, said spring being so constructed and arranged as to move said support piece to its retracted position when said pin is withdrawn.

* * * * *